(12) United States Patent
Graff et al.

(10) Patent No.: US 6,846,807 B1
(45) Date of Patent: Jan. 25, 2005

(54) COLORECTAL NEOPLASIA PROPHYLAXIS

(75) Inventors: Jonathan Graff, Dallas, TX (US);
Matthew Wieduwilt, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/627,451

(22) Filed: Jul. 25, 2003

(51) Int. Cl.[7] .................. A61K 31/70; A61K 31/37
(52) U.S. Cl. ..................... 514/39; 514/2; 514/414; 514/183; 514/359; 514/408; 514/410; 514/412; 536/18.7; 536/22.1; 536/23.1; 435/4; 435/6; 435/325; 435/41; 435/63; 424/156.1; 424/155.1; 424/243
(58) Field of Search .............. 514/39, 2, 414, 514/183, 359, 408, 410, 412; 536/18.7, 22.1, 23.1; 435/4, 6, 325, 41, 63; 424/156.1, 155.1, 243

(56) References Cited

U.S. PATENT DOCUMENTS 5,614,502 A * 3/1997 Flotte et al. ............... 514/34
6,482,802 B1 * 11/2002 Hu et al. ................... 514/39

* cited by examiner

*Primary Examiner*—James O. Wilson
*Assistant Examiner*—Devesh Khare
(74) *Attorney, Agent, or Firm*—Richard Aron Osman

(57) ABSTRACT

Development of colorectal neoplasia in a patient subject or predisposed to colorectal neoplasia is reduced by the steps of (a) determining a patient is subject or predisposed to colorectal neoplasia; and (b) enterically delivering into the gut of the person an effective amount of an aminoglycoside antibiotic having poor gut absorption, whereby the development of the colorectal neoplasia is reduced as compared with otherwise similar non-treated patients.

16 Claims, No Drawings

COLORECTAL NEOPLASIA PROPHYLAXIS

FIELD OF THE INVENTION

The field of this invention is use of aminoglycoside antibiotics to reduce development of colorectal neoplasia.

BACKGROUND OF THE INVENTION

Aminoglycosides are potent bactericidal antibiotics, particularly active against aerobic, gram-negative bacteria and act synergistically against certain gram-positive organisms. Gentamicin is the most commonly used aminoglycoside, but amikacin may be particularly effective against resistant organisms. Aminoglycosides are used in the treatment of severe infections of the abdomen and urinary tract, as well as bacteremia and endocarditis. Aminoglycosides are poorly absorbed from the gastrointestinal tract. After parenteral administration, aminoglycosides are primarily distributed within the extracellular fluid. Penetration of biologic membranes is poor because of the drug's polar structure, and intracellular concentrations are usually low, with the exception of the proximal renal tubule; for review, see, Gonzalez et al., American Family Physician, Nov. 15, 1998; The Merck Manual of Diagnosis and Therapy, 1999, $17^{th}$ Ed, Chap. 153.

Hu (1998, PNAS 95, 9791–795) and Hu et al. (U.S. Pat. No. 6,482,802) report that neomycin was the only member of a panel of aminoglycoside antibiotics that was able to reduce angiogenin-induced cell proliferation and angiogenesis, as measured using cultured human endothelial cells and chick embryo chorioallantoic membranes (CAM). Streptomycin, kanamycin, gentamicin, amikacin, and paromomycin were found to lack anti-angiogenic activity. This Hu attributes to phospholipase C (PLC) inhibition because neomycin is the only aminoglycoside antibiotic of the panel tested that inhibits PLC, and because U-73122, another PLC inhibitor, similarly inhibited angiogenin-induced cell proliferation and angiogenesis. See abstract of Hu paper; col. 20, lines 22–28, col. 21, line 66—col. 22, line 8, and col. 27, lines 8–27 of Hu patent. The Hu patent also reports that injected neomycin was able to reduce growth of cultured angiogenin-secreting tumor cells (Olson et al., Int J Cancer. 2002 Apr. 20;98:923–9; Clin Cancer Res. 2001 November;7:3598–605) transplanted into mice; see, col. 27, line 43—col. 29, line 10 of Hu patent.

From these findings, Hu suggests use of neomycin for treating any angiogenin-induced angiogenesis. The Hu patent purports applicability to all angiogenesis-related diseases, which are "myriad and varied" and "include, but are not limited to, various forms of neovascularization or hypervascularization diseases, inflammatory diseases, arthritis and cancer", and: then goes on to recite a laundry-list of all major solid and blood-borne tumors, corneal and retinal diseases, inflammatory diseases, and various infectious diseases, including AIDS (col. 16, line 56—col. 18, line 16). Among the 60+ recited solid tumors is colon cancer (col. 17, lines 10–11).

Hu does not provide the public with any cure for cancer, inflammatory disease, arthritis, or AIDS. He has shown that neomycin can reduce angiogenin-induced angiogenesis and growth in CAM and cultured cell models, and from these data, claims to be able to treat innumerable human diseases. In fact, anti-angiogenesis drugs have notoriously failed to live up to their promise as cancer therapies, primarily because there are dozens of alternative factors which can drive angiogenesis. Science Journal, WSJ, Jul. 11, 2003. Furthermore, reports using azoxymethane (AOM) and 1,2-dimethyl hydrazine (DMH)-induced colon cancers have suggested neomycin is not a viable therapy for colon cancer, and may actually increase the incidence of colon adenocarcinomas (Reddy et al., 1984 JNCI 73, 275–9; Panda et al., 1999, Br J Cancer 80, 1132–6).

With the recent development of colon cancer animal models based on defined genetic lesions (e.g. Zhu et al., Cell 1998, 94, 703–714), the use of chemical carcinogenesis models like AOM and DMH has become less favored (Boivin et al., Gastroenterology 2003, 124, 762–777). Hence, a recent review of colon cancer chemoprevention surveys the many agents reported to influence intestinal tumors, and does not include any antibiotics; see, Table 1 of Corpet et al., Cancer Epidemiology, Biomakers & Prevention 2003, 12, 391–400. Work in colon cancer animal models has suggested that intestinal neoplasia is independent of gut microbial status (Dove et al., Cancer Res 1997, 57, 812–14).

The present inventors made the serendipitous discovery that enterically delivered aminoglycoside antibiotics can dramatically reduce the development of colorectal carcinogenesis in defined rodent models. The inventors here clinically extend these animal model findings by showing that enterically delivered aminoglycoside antibiotics can inhibit large bowel carcinogenesis in human patients with familial adenomatous polyposis. The inventors further extend these findings by showing that altering the population profile of gut flora, through a defined regimen of aminoglycoside antibiotic treatment and supplementation of non-target gut microbes such as Lactobacillus, is effective in preventing the formation of colorectal polyps and colorectal cancer. The inventors demonstrate prevention of spontaneous tumor formation indicating that the disclosed protocols interfere with early processes of carcinogenesis that are distinct from angiogenesis.

SUMMARY OF THE INVENTION

The invention provides methods and compositions for reducing development of colorectal neoplasia in a patients subject or predisposed to colorectal neoplasia The general methods comprise the steps of (a) determining a patient is subject or predisposed to colorectal neoplasia; and (b) enterically delivering into the gut of the person an effective amount of an aminoglycoside antibiotic having poor gut absorption, whereby the development of the colorectal neoplasia is reduced as compared with otherwise similar non-treated patients.

Colorectal neoplasias encompass large intestine, bowel, colon and rectal neoplasias, including colorectal neoplasias that are non-angiogenin secreting and/or non-angiogenin dependent. Preferred target patients have undergone removal or ablation of a colorectal neoplasia and are determined to be predisposed to colorectal neoplasia recurrence, including patients having a known predisposition, particularly a genetic predisposition, due to familial history of colon cancer, especially in association with a known syndrome such as familial adenomatous polyposis or hereditary non-polyposis colon cancer. Hence, the determining step may comprise detecting an indication of or predisposition to polyps or colorectal cancer.

The recited aminoglycoside antibiotic may be one of a plurality of different antibiotics, particularly different aminoglycoside antibiotics, and the delivering step may be effected by delivering the antibiotics in periodic dosages of different subsets of the antibiotics. The methods may further comprise introducing into the gut an effective amount of a probiotic, gut-beneficial microbial culture, such as species of *Lactobacillus, Bifidobacteria, Bacteroides, Streptococcus*, and *Saccharomyces*.

The invention also provides kits specifically tailored for the subject methods, for delivering an aminoglycoside antibiotic having poor gut absorption. Typically, such kits comprise an aminoglycoside antibiotic having poor gut absorption, and an associated instructional medium describing use of the antibiotic in a subject method. The kits may include varying doses of the aminoglycoside antibiotic, alone or in combination with another antibiotic or a defined dose of a probiotic, gut-beneficial microbe such as *Lactobacillus*.

DESCRIPTION OF PARTICULAR EMBODIMENTS OF THE INVENTION

The invention provides methods and compositions for reducing development of colorectal neoplasia in patients, particularly patients known to be subject or predisposed to colorectal neoplasia. The general methods comprise the steps of (a) determining a patient is subject or predisposed to colorectal neoplasia; and (b) enterically delivering into the gut of the person an effective amount of an aminoglycoside antibiotic having poor gut absorption, whereby the development of the colorectal neoplasia is reduced as compared with otherwise similar non-treated patients.

Colorectal neoplasias of the invention include neoplasias of the colon, bowel, rectum or large intestine, particularly adenomatous polyps and colon carcinoma. In particular embodiments, the colorectal neoplasia is non-angiogenin secreting and/or non-angiogenin dependent. In particular embodiments, the subject patient has undergone removal or ablation of a colorectal neoplasia and is determined to be predisposed to colorectal neoplasia recurrence, including genetically predisposed to the development of colorectal neoplasia.

Preferred target patients are predetermined to have a personal or familial history of colorectal neoplasia, or are predetermined to be at relatively high risk of developing a colorectal neoplasia. Hence, the determining step may comprise detecting an indication of or predisposition to polyps or colorectal cancer. In a particular embodiment, the invention reduces the risk of reccurrence of colorectal neoplasia.

Exemplary aminoglycoside antibiotics useful in the invention include Amikacin (Amikin®), Gentamicin (Garamycin®), Kanamycin (Kantrex®), Neomycin (Mycifradin®), Netilmicin (Netromycin®), Paromomycin (Humatin®), Streptomycin, and Tobramycin (TOBI Solution®, TobraDex®, Nebcin®). However, the methods may be practiced with alternative aminoglycosides which function similarly, which is readily determined empirically, such as in the animal models described below. In a particular embodiment, the administered aminoglycoside antibiotic is other than neomycin.

In a particular embodiment, the aminoglycoside antibiotic is one of a plurality of different antibiotics, preferably including or being different aminoglycoside antibiotics, and the delivering step is effected by delivering the antibiotics in periodic dosages of different subsets of the antibiotics. Optimal dosages are readily determined empirically as exemplified below and the invention has been documented with numerous example of known safe and intestinally-effective oral dosages of subject antibiotics.

The invention has been documented with a variety of aminoglycoside antibiotics, however alternative antibiotics may be substituted in the same methods so long as they provide the requisite reduction in the development of colorectal cancer, assayed as described below, and preferably provide poor gut absorption, similar to aminoglycoside antibiotics, such as neomycin. Furthermore, methods for modifying or delivering otherwise highly gut absorbable antibiotics to or in a poorly gut absorbable form are known in the art, and include gut-retaining chemical moieties, chelators, enteric coatings, etc.; see, *Remington's Pharmaceutical Science*, Mack Publishing Co, NJ (1991). In addition, suitable excipients or carriers and methods for preparing administrable compositions are known or apparent to those skilled in the art and are described in more detail in publications such as *Remington's*.

The invention also provides embodiments which forestall or help avoid development of undesirable effects of antibiotic usage, such as side-effects, antibiotic resistance, etc. These embodiments adopt established procedures for minimizing development of side effects, resistance, etc. For example, administered antibiotics may be administered in punctuated and/or sequential dosage regimes. In a particular embodiment, a plurality of different antibiotics are administered in sequential dosage regimes, alternating exposures to each antibiotic over time. Hence, the antibiotics may be provided in a cyclic dispenser and/or with instructions providing a dosage regime of a first antibiotic or cocktail, followed by a second dosage regime of a second, different antibiotic or cocktail, etc. In a particular embodiment, the dispensers are designed like conventional birth control pill dispensers, wherein the composition of the pills differs over time and they are taken in a specific sequence for a defined period, after which the cycle just starts over again.

In particular embodiments, the invention further comprises introducing into the gut an effective amount of a probiotic, gut-beneficial microbial culture. A wide range of gut-beneficial microbes are known in the art, including species of *Lactobacillus, Bifidobacteria, Bacteroides, Streptococcus*, and *Saccharomyces*. Exemplary well-known species include *L. acidophilus, L. reuteri, L. acidophilus, L. bulgaricus, L. plantarum, L. casei, L. gasseri*, L. GG, *S. thermophilus, S. salivarius, B. bifidus*, and *Saccharomyces boulardii*. The probiotic microbes are typically administered orally, typically in a defined dosage regime. The microbe may be one of a plurality of different microbes, and the delivering step is effected by delivering the microbes in periodic dosages of different subsets of the antibiotics, or in cocktails or mixtures of different sets or subsets of various microbes. For example, in one embodiment dosages are provides by capsules containing a combination of *L. fermentum* RC-14 and *L. rhamnosus* GR-1 and/or *L. rhamnosus* GG in freeze-dried form (a total of $>10^9$ viable bacteria). The probiotics may be administered in the context of a periodic or changing antibiotic dosage regime, such as described above.

The invention also provides kits specifically tailored to practicing the subject methods. In one embodiment, the kits are constructed for delivering an aminoglycoside antibiotic having poor gut absorption, and comprise an aminoglycoside antibiotic having poor gut absorption, typically in premeasured, defined dosages, and an associated instructional medium describing use of the antibiotic in a subject method.

EXAMPLES

In the following examples, we demonstrate that orally-delivered aminoglycosides reduce development of colorectal neoplasia.

I. Orally-delivered aminoglycosides reduce development of colon cancer in animal models predisposed to colon neoplasia. Smad3 mutant and APC/MIN mice are fed on a standard laboratory diet, with aminoglycoside antibiotics added to the water. For example, 4 ml neomycin sulfate (BIOSOL, Pharmacia & Upjohn Company) was diluted in 500 ml sterile drinking water to give a final concentration of 1.6 mg/ml neomycin sulfate (1.1 mg/ml neomycin). Metronidazole was diluted in sterile drinking water to a final concentration of 0.5 mg/ml. The same concentrations are used for either combined or separate drug trials.

Smad3 mutant mice are maintained in 129Sv strain; APC/MIN mice are maintained in C57BL/6J. Both Smad3 mutant and APC/MIN mice are started on antibiotics at 5 weeks of age (range: 4–6 weeks). Mice are monitored and scored for survival and visible rectal tumors. Mice are sacrificed when showing severe distress (typically rectal prolapse with significant dehydration,. hypokinesis, cachexia). At sacrifice mice are dissected and their overall state assessed. Large intestines were harvested, opened longitudinally, and tumor number, location, and size recorded. Note that Smad3 mutant mice comprise an operable neo-resistance gene; hence, any neomycin absorbed from their gut should be inactivated.

Approximately 90% of control Smad3 mutant mice develop colorectal cancer within seven months. However, orally delivered aminoglycosides (amikacin, gentamicin, kanamycin, netilmicin, paromomycin, streptomycin, and tobramycin) prevent tumor development in over 90% of our Smad3 mice. For example, 9 of 10 untreated mice developed colorectal tumors within 24 weeks (i.e., by the age of 24 weeks). Oral treatment with neomycin however, prevented the development of tumors in 11 of 12 mice at 24 weeks. We find similar reductions in colon cancer development across the tested aminoglycosides in both Smad3 mutant and APC/MIN mice. In contrast, a metronidazole treatment group was not significantly different from non-treated controls.

II. Orally-delivered aminoglycosides reduce development of colorectal polyps in patients with familial adenomatous polyposis. In this study we demonstrate the efficacy of aminoglycoside antibiotices on colorectal polyps in patients with familial adenomatous polyposis. We adapted the double-blind, placebo-controlled study format of Steinbach et al., 2000, NEJM, 342:1946–1952 to randomly assign patients to one of four treatment groups (neomycin or paramomycin, at 1 or 2 g daily in orally administered capsules) or a placebo group for six months. All patients undergo endoscopy at the beginning and end of the study. The number and size of polyps is determined from photographs and videotapes; the response to treatment is expressed as the mean percent change from base line.

Results: At base line, the mean (±SD) number of polyps in focal areas where polyps are counted is similar (about 10±10) in patients assigned to placebo or treatment groups. After six months, the patients receiving 1 or 2 g/day of either neomycin or paramomycin have about a 30 percent reduction in the mean number of colorectal polyps and a 30 percent reduction in the polyp burden (the sum of polyp diameters), whereas the placebo group does not exhibit a: significant reduction. The improvement in the extent of colorectal polyposis in the treatment groups is confirmed by a panel of endoscopists who independently review the videotapes. The incidence of adverse events was similar among the groups.

Conclusion: In patients with familial adenomatous polyposis, six months of daily treatment with 1 or 2 g of either neomycin or paramomycin leads to a significant reduction in the number of colorectal polyps.

III. Orally-delivered aminoglycosides reduce development of colorectal adenomas in patients with previous colorectal cancer. In this study, we demonstrate the efficacy of orally-delivered aminoglycosides on the incidence of colorectal adenomas. We adapted the double-blind, placebo-controlled trial format of Sandier, et al. 2003, NEJM 348, 883–90 to randomly assign patients with prior colorectal cancer to one of four treatment groups (neomycin or paramomycin, at 1 or 2 g daily in orally administered capsules) or a placebo group for six months. We determine the proportion of patients with adenomas, the number of recurrent adenomas, and the time to the development of adenoma between randomization and subsequent colonoscopic examinations. Relative risks are adjusted for age, sex, cancer stage, the number of colonoscopic examinations, and the time to first colonoscopy.

Assigned patients have had at least one colonoscopic examination a median of 12 months after randomization. One or more adenomas are found in approximately 10 percent of patients in the four treatment groups and about 30 percent of patients in the placebo group. The mean number of adenomas is also lower in all four treatment groups than the placebo group. Hence, the average, adjusted relative risk of any recurrent adenoma in the treatment groups, as compared with the placebo group, was about 0.5. The time to the detection of a first adenoma is also longer in each treatment group than in the placebo group.

Conclusion: We find that daily use of 1 or 2 g of either neomycin or paramomycin decreases the occurrence of new colorectal adenomas among patients with a history of colorectal cancer.

The foregoing descriptions of particular embodiments and examples are offered by way of illustration and not by way of limitation. Unless contraindicated or noted otherwise, in these descriptions and throughout this specification, the terms "a" and "an" mean one or more, the term "or" means and/or.

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of reducing development of colorectal neoplasia in a patient subject or predisposed to colorectal neoplasia, the method comprising the steps of:

determining a patient is subject or predisposed to colorectal neoplasia; and enterically delivering into the gut of the person an effective amount of an aminoglycoside antibiotic having poor gut absorption, whereby the development of the colorectal neoplasia is reduced as compared with otherwise similar non-treated patients.

2. The method of claim 1, wherein the colorectal neoplasia is non-angiogenin secreting or non-angiogenin dependent.

3. The method of claim 1, wherein the colorectal neoplasia is adenomatous polyps.

4. The method of claim 1, wherein the colorectal neoplasia is hereditary non-polyposis colon cancer.

5. The method of claim 1, wherein the patient has undergone removal or ablation of a colorectal neoplasia and is determined to be predisposed to colorectal neoplasia recurrence.

6. The method of claim 1, wherein the aminoglycoside antibiotic is selected from the group consisting of: Amikacin (Amikin®), Gentamicin (Garamycin®), Kanamycin (Kantrex®), Neomycin (Mycifradin®), Netilmicin (Netromycin®), Paromomycin (Humatin®), Streptomycin, and Tobramycin (TOBI Solution®, TobraDex®, Nebcin®).

7. The method of claim 1, wherein the aminoglycoside antibiotic is other than neomycin.

8. The method of claim 1, wherein the aminoglycoside antibiotic is one of a plurality of different antibiotics, and the delivering step is effected by delivering the antibiotics in periodic dosages of different subsets of the antibiotics.

9. The method of claim 1, wherein the aminoglycoside antibiotic is one of a plurality of different antibiotics, and the delivering step is effected by delivering the antibiotics in periodic dosages of different subsets of the antibiotics, wherein the different antibiotics are aminoglycoside antibiotics.

10. The method of claim 1, wherein the aminoglycoside antibiotic is one of a plurality of different antibiotics, and the delivering step is effected by delivering the antibiotics in periodic dosages of different subsets of the antibiotics, wherein the method further comprises introducing into the gut an effective amount of probiotic, gut-beneficial microbial cultures in periodic dosages.

11. The method of claim 1, wherein the determining step is done by detecting an indication of or predisposition to polyps or colorectal cancer.

12. The method of claim 1, wherein the delivering step is effected by delivering a constant over time dosage of the aminoglycoside.

13. The method of claim 1, wherein the delivering step is effected by delivering a varying over time dosage of the aminoglycoside.

14. The method of claim 1, wherein the method further comprises introducing into the gut an effective amount of a probiotic, gut-beneficial microbial culture.

15. The method of claim 1, wherein the gut-beneficial culture comprises a microbe selected from the group consisting of *Lactobacillus, Bifidobacteria, Bacteroides, Streptococcus*, and *Saccharomyces*.

16. The method of claim 1, wherein the gut-beneficial culture comprises a microbe selected from the group consisting of: *L. acidophilus, L. reuteri, L. acidophilus, L. bulgaricus, L. plantarum, L. casei, L. gasseri,* L. GG, *S. thermophilus, S. salivarius, B. bifidus*, and *Saccharomyces boulardii*.

* * * * *

UNITED STATES PATENT AND TRADEMARK OFFICE
CERTIFICATE OF CORRECTION

PATENT NO. : 6,846,807 B1  
DATED : January 25, 2005  
INVENTOR(S) : Jonathan Graff and Matthew Wieduwilt Page 1 of 1

It is certified that error appears in the above-identified patent and that said Letters Patent is hereby corrected as shown below:

Column 6,
Line 56, the "determining" step should read -- determining a patient is subject to colorectal neoplasia, or has undergone removal or ablation of a colorectal neoplasia; and --

Column 7, lines 1-27 and Column 8, lines 1-11,
Claims 5, 6, 12 and 13 should read as follows:

5. The method of claim 1, wherein the patient has undergone removal or ablation of a colorectal neoplasia.

6. The method of claim 1, wherein the aminoglycoside antibiotic is selected from the group consisting of: Amikacin, Gentamicin, Kanamycin, Neomycin, Nelilmicin, Paromomycin, Streptomycin, and Tobramycin.

12. The method of claim 1, wherein the delivering step is effected by delivering a constant dosage of the aminoglycoside.

13. The method of claim 1, wherein the delivering step is effected by delivering a varying dosage of the aminoglycoside.

Signed and Sealed this

Third Day of May, 2005

JON W. DUDAS  
*Director of the United States Patent and Trademark Office*